United States Patent
Walsdorf, Sr. et al.

(10) Patent No.: US 6,887,897 B2
(45) Date of Patent: May 3, 2005

(54) CALCIUM GLUTARATE SUPPLEMENT AND PHOSPHORUS BINDER

(75) Inventors: Neill B. Walsdorf, Sr., San Antonio, TX (US); George Alexandrides, San Antonio, TX (US)

(73) Assignee: Mission Pharmacal Company, San Antonio, TX (US)

( * ) Notice: Subject to any disclaimer, the term of this patent is extended or adjusted under 35 U.S.C. 154(b) by 0 days.

(21) Appl. No.: 09/919,025

(22) Filed: Jul. 31, 2001

(65) Prior Publication Data

US 2003/0077331 A1 Apr. 24, 2003

(51) Int. Cl.$^7$ ............... A61K 31/28; A61K 31/194
(52) U.S. Cl. ............... 514/492; 514/557; 514/574; 514/578; 514/891
(58) Field of Search ............... 424/451, 464, 424/43, 682, 490; 514/492, 557, 574, 578, 891, 54, 60

(56) References Cited

U.S. PATENT DOCUMENTS

| | | | |
|---|---|---|---|
| 3,887,533 A | 6/1975 | Mukerjee | 260/88.2 |
| 4,308,264 A | 12/1981 | Conway et al. | 424/236 |
| 4,689,322 A * | 8/1987 | Kulbe et al. | 514/54 |
| 4,772,467 A | 9/1988 | Pak | 424/127 |
| 4,814,177 A | 3/1989 | Walsdorf et al. | 424/464 |
| 4,851,221 A | 7/1989 | Pak et al. | 424/693 |
| 4,870,105 A | 9/1989 | Fordtran | 514/557 |
| 5,039,668 A | 8/1991 | Colina | 514/52 |
| 5,075,499 A | 12/1991 | Walsdorf et al. | 562/590 |
| 5,143,732 A | 9/1992 | Helbig et al. | 424/647 |
| 5,405,308 A | 4/1995 | Headley et al. | 494/67 |
| 5,432,200 A | 7/1995 | Walsdorf et al. | 514/574 |
| 5,514,281 A | 5/1996 | Boos et al. | 210/645 |
| 5,597,815 A | 1/1997 | Deluca | 514/167 |
| 5,746,818 A | 5/1998 | Yatake | 106/31.86 |
| 5,753,706 A | 5/1998 | Hsu | 514/578 |
| 5,879,698 A | 3/1999 | Ellenbogen et al. | 424/440 |
| 5,900,255 A | 5/1999 | Ohta et al. | 424/602 |
| 5,919,491 A | 7/1999 | Adusumilli et al. | 424/678 |
| 5,939,406 A | 8/1999 | DeLuca et al. | 514/167 |
| 5,952,308 A | 9/1999 | Nakanishi et al. | 514/25 |
| 6,004,389 A | 12/1999 | Yatake | 106/31.86 |
| 6,048,901 A | 4/2000 | Cleveland et al. | 514/723 |
| 6,077,557 A | 6/2000 | Gordon et al. | 426/573 |
| 6,077,872 A | 6/2000 | Yu et al. | 514/663 |
| 6,080,431 A | 6/2000 | Andon et al. | 424/602 |
| 6,103,126 A | 8/2000 | Boos et al. | 210/645 |
| 6,103,709 A | 8/2000 | Norman et al. | |
| 6,160,016 A | 12/2000 | DeLuca | 514/557 |
| 6,187,741 B1 | 2/2001 | Farbood et al. | 512/25 |
| 6,190,702 B1 | 2/2001 | Takado et al. | 424/501 |

OTHER PUBLICATIONS

Remington's Pharmaceutical Sciences (1985), pp. 1492, 1603, 1607, 1625.*
WEST online, file DWPI, RO 87637 (1985), Abstract.*
STN/CAS onine, file CAPLUS, CN 1210695 (1999), Abstract.*

* cited by examiner

*Primary Examiner*—S. Mark Clardy
*Assistant Examiner*—Frank Choi
(74) *Attorney, Agent, or Firm*—Fulbright & Jaworski LLP

(57) ABSTRACT

Methods of controlling calcium intake and phosphate metabolism and metabolic acidosis in patients suffering from renal failure and associated hyperphosphatemia or patients predisposed to development of a hyperphosphatemic condition are provided. The method in accordance with this invention comprises administering to a patient a calcium glutarate compound. Therapeutic benefit can be realized in accordance with such method by administering the compound orally to a patient to increase available calcium and contact and bind with ingested phosphate in the patient's digestive tract, and thereby prevent its intestinal absorption.

26 Claims, No Drawings

CALCIUM GLUTARATE SUPPLEMENT AND PHOSPHORUS BINDER

FIELD OF THE INVENTION

The present invention relates generally to calcium supplementation and controlling phosphate retention and particularly, to methods for treating patients on dialysis and suffering from renal failure and associated hyperphosphatemia.

BACKGROUND OF THE INVENTION

Phosphorus is the sixth most abundant element in the human body. It is critical for bone mineralization, cellular structure, genetic coding, and energy metabolism. Many organic and inorganic forms exist. Approximately 1,000 g of phosphorus is present in an adult, of which 80–90% is in bone. An additional 10–14% is intracellular and the remaining 1%, is extracellular.

The phosphorus in plasma is 12–17% protein bound. Free serum compounds represent much less than 1% of the total body phosphorus content. This fraction also varies with shifts between the intracellular and extracellular compartments. Thus, serum phosphorus levels may not accurately reflect the total body phosphorus content.
Levels are expressed in terms of serum phosphorus mass (mg/dL). One mg/dL of phosphorus is equal to 0.32 mmol of phosphate. The normal adult range is 2.5 to 4.5 mg/dL (0.81 to 1.45 mmol/L). Levels are 50% higher in infants and 30% higher in children due to growth hormone effects. Hyperphosphatemia is an abnormally elevated serum phosphate level. Normal serum phosphate levels are in the range of 2.5 to 4.5 mg/dl.

Significant hyperphosphatemia is considered present when levels are greater than 5 mg/dL in adults or 7 mg/dL in children or adolescents.

Phosphorus homeostasis is normally maintained through several mechanisms. Renal excretion equals gastrointestinal (GI) absorption. Cellular release is balanced by uptake in other tissues. Hormonal control is mainly provided by parathyroid hormone. Hyperphosphatemia occurs when phosphorus load (from GI absorption, exogenous administration, or cellular release) exceeds renal excretion and tissue uptake.

Phosphorus is present in nearly all foods, and GI absorption of dietary forms is very efficient. With low dietary intake, 80–90% is absorbed. When it is greater than 10 mg/kg daily, 70% is absorbed. Normal daily dietary intake varies from 800–1,500 mg. Absorption occurs mainly in the jejunum, although some is present throughout the remainder of the intestinal tract. A small amount of GI secretion occurs.

Serum phosphorus levels rise easily after a large meal. Antacids can decrease absorption as calcium, aluminum and magnesium bind phosphorus into insoluble complexes. Aluminum is an efficient binder but is considered less desirable.

Renal phosphorus excretion normally matches the amount of daily GI absorption. This occurs in the proximal tubule, and is mainly dependent on the filtered phosphorus load. And, as the filtered load increases, a higher fraction is reabsorbed. The converse is also true.

Reabsorption is dependent on concurrent sodium transport. Sodium not reabsorbed at the proximal tubule may be reabsorbed distally. This does not occur for phosphorus. Proximal diuretics, which decrease sodium reabsorption, also increase phosphorus excretion. The usual load excreted is 5–15% of the filtered load or 600–800 mg/d in the normal net steady state. This amount may increase markedly in hyperphosphatemia. It is unusual to have marked hyperphosphatemia in chronic renal insufficiency until the glomerular filtration rate (GFR) is less than 25 mL/min. Secretion plays an insignificant role in renal phosphorus excretion.

Hyperphosphatemia is most often found in association with renal insufficiency. Most patients with acute or chronic renal failure have hyperphosphatemia in some degree. To avoid hyperphosphatemia, patients with end-stage renal disease must restrict dietary phosphorus and must take oral phosphate binders to reduce absorption. Severe hyperphosphatemia is rare. The only direct effect of hyperphosphatemia is that of metastatic calcification, in which deposits of calcium phosphate accumulate in soft tissues, including the heart, lungs, blood vessels, kidneys, brain, eyes, periarticular tissues, and skin. The risk increases when hyperphosphatemia is present for an extended period and when the calcium (mg/dL)-phosphate (mg/dL) product exceeds 70.

In severe metastatic calcification (calciphylaxis), blood vessel deposits may lead to gangrene of the extremities. If the hyperphosphatemia is corrected, there is some reversal of the process. Protracted hyperphosphatemia contributes to renal osteodystrophy in patients with chronic renal insufficiency. Hyperphosphatemia causes hypocalcemia by precipitating calcium, decreasing vitamin D production and interfering with parathyroid hormone-mediated bone resorption. Severe life-threatening hypocalcemia may result. Symptoms and signs of acute hyperphosphatemia are due to the effects of hypocalcemia.

In the United States the 250,000 patients with end-stage renal disease make up the bulk of patients with hyperphosphatemia. Although women have physiologic elevation of serum phosphate levels after menopause, this has no clinical significance. Phosphorus levels are naturally higher in infants, children, and postmenopausal women. A phosphate-driven rise in children of erythrocyte 2,3-DPG and ATP may account for the physiologic anemia of childhood.

Phosphorus retention plays a major role in chronic renal failure in the development of both secondary hyperparathyroidism and osteodystrophy. Bricker, N., S. et al., *Archives of Internal Medicine* 123:543–553 (1969); Rubini, M. E. et al., *Archives of Internal Medicine* 124:663–669 (1969); Slatopolsky, E., et al., *Journal of Clinical Investigation* 50:492–449 (1971); Bricker, N. S., *New England Journal of Medicine* 286:1093–1099 (1972); Slatopolsky, E. S., et al., *Kidney Int.* 2:147–151 (1972). Phosphate is primarily excreted through the kidney. Phosphate retention therefore inevitably occurs in renal failure. Phosphate restriction plays an important role in slowing down deterioration of renal function as well as soft tissue calcification in renal failure. A high intake of dietary phosphorus in experimental renal failure worsens renal function (Haut, L. L., *Kidney Int* 17:722–731 (1980); Karlinsky, D. et al., *Kidney Int* 17:293–302 (1980)) and a low phosphate intake arrests progression of chronic renal failure. Lumlertgul, D. et al., *Kidney Int* 29:658–666 (1986). Studies have demonstrated that phosphate restriction either increases plasma calcitriol (the most potent vitamin D metabolite) and suppresses secondary hyperparathyroidism (Portale, A. A. et al., *J. Clin. Invest* 73:1580–1589 (1989); Kilav, R. et al., *J Clin. Invest* 96:327–333 (1995); Lopez, H. et al., *Am. J Physiol* 259:F432–437 (1990)), or directly inhibits parathyroid cell proliferation. Naveh-Many, T. et al., *Am. Soc. Nephrol* 6:968 (1995). Taken together, maintaining a normal plasma concentration and tissue content of phosphate is an important means to prevent secondary hyperparathyroidism, renal osteodystrophy and soft tissue calcification in renal failure.

Dietary restriction of phosphate is difficult to achieve and thrice weekly dialysis alone does not remove daily absorbed phosphate. Therefore, phosphate binding agents have generally been employed to control phosphate metabolism in renal failure. In the past nephrologists have used aluminum carbonate or aluminum hydroxide as phosphate binding agents. Concerns about aluminum toxicity in renal failure have prompted increased use of calcium carbonate and calcium acetate and a cessation in the use of aluminum compounds. However, calcium carbonate or other known calcium preparations that bind phosphate may be inadequate to remove all the ingested dietary phosphate. Some may also provide too much calcium to end stage renal disease (ESRD) patients.

Animal studies have demonstrated that while both aluminum and ferric salts reduce plasma phosphate and urinary phosphate excretion, they also drastically reduced bone ash and bone phosphorus. Cox, G. et al., *J. Biol. Chem* 92:Xi–Xii (1931). For example, growing rats fed with ferric salts had growth retardation, hypophosphatemia, considerable loss of bone ash and total body content of calcium and phosphorus. The rats developed rickets within one month in severe phosphate restriction. Brock, J. et al., *J. Pediat* 4:442–453 (1934); Rehm, P. et al., *J. Nutrition* 19:213–222 (1940). Ferric salts also produced severe rickets and hypophosphatemia in one-day old chicks. Deobald, H. et al., *Am. J. Physiol* 111:118–123 (1935).

Antacids have been used to bind dietary phosphorus to prevent phosphorus retention and prevent its absorption. This process is referred to as phosphorus binding and appears to be a chemical reaction between dietary phosphorus and the cation present in the binder compound, which is usually albumin or calcium. The binding results in the formation of insoluble and unabsorbable phosphate compounds, adsorption of phosphorus ions on the surface of binder particles, or a combination of both.

Antacids are inefficient at binding phosphorus in vivo. For example, a study by Ramirez, et al., noted that even though aluminum-containing or calcium-containing antacids were administered in large excess, they bound only 19–35 percent of dietary phosphors. Ramirez, J. A., et al., Kidney Int. 30:753–759 (1986). Similar conclusions can be derived from data presented in earlier studies. Kirsner, J. B., Journal of Clinical Investigation, 22:47–52 (1943); Clarkson, E. M., et al., Clinical Science 43:519–531 (1972); Cam, J. M., et al., Clinical Science and Molecular Medicine 51:407–414 (1976); Man, N. K. et al., Proceedings of the European Dialysis and Transplantation Association 12:245–55 (1975).

The inefficiency of commonly used phosphorus binders creates a clinical dilemma. The dose of the binder must be increased to control hyperphosphatemia, but increased risk of toxicity or other undesirable side affects of the binder results from the increased dose. This toxicity may include bone disease and aluminum dementia from aluminum-containing antacids and hypercalcemia and soft tissue calcification from calcium-containing antacids. These risks are particularly problematic in patients with chronic renal disease.

It is well known that patients with chronic renal insufficiency can be successfully treated for years with the aid of dialysis (hemodialysis or peritoneal dialysis or artificial kidney) and thus be kept alive for a long time period. Substances usually eliminated with the urine are removed by the artificial kidney over a semi-permeable membrane. The quality and quantity of substance transport in this process is determined by a number of factors such as the surface area, the structure and thickness of the dialysis membrane, the flow rates of the washing solution (dialysis fluid) and of the blood, the ultra-filtration rate, the duration of the dialysis treatment, the difference in concentration of the dialyzable substances between blood and washing solution as well as the molecular size and form of the dialyzable substances.

However, during the course of a long-term hemodialysis complications often occur which are characteristic for this group of patients. Thus renal osteodystrophy is one of the serious longterm complications. This disease not only considerably impairs the general state of health of the dialysis patient but he is additionally also threatened with invalidity. One component of this clinical picture is secondary hyperparathyroidism which is associated with uremic hyperphosphatemia. The chronic accumulation of phosphate in dialysis patients leads to highly increased serum concentrations of inorganic phosphorus (more than 6 mg/dl) and is due to reduced phosphate clearance by the dialysis membrane.

A primary aim of prophylactic and therapeutic measures in patients with renal osteodystrophy is therefore to lower the level of serum phosphate below a threshold value of 1.8 mmol/1 (5.6 mg phosphorus/dl). A dietary restriction of the phosphate intake and thereby an effective lowering of the level of serum phosphate is limited if not impossible in long-term therapy since there is the risk of an inadequate protein intake and thus of malnutrition. Thus for example on an average dietary phosphate intake of 3.8 to 4.7 g/day only about 1 g phosphate per day can be eliminated by dialysis (hemodialysis or peritoneal dialysis). Thus the patients have an undesired positive phosphate balance despite the restriction (Hercz, G. et al., Kidney Int. Suppl. 22 (1987), 215–220).

For this reason phosphate binding agents that can be administered orally are preferably used as therapeutic agents which are intended to prevent the resorption of food phosphates in the gastrointestinal tract. Known substances with phosphate-binding properties are the calcium salts calcium acetate, calcium carbonate, calcium citrate, calcium alginate, calcium gluconate, calcium lactate and calcium sulfate, magnesium carbonate and magnesium hydroxide as well as aluminum hydroxide and aluminum carbonate. However, not all of these salts have gained therapeutic importance or been considered safe or efficacious. Aluminum hydroxide, calcium carbonate and calcium acetate have been used. However, these agents for enteric phosphate restriction may have undesired side effects. Thus when $Al^{3+}$ compounds are administered chronically a microcytic anemia or encephalopathy can develop with a very poor prognosis or osteopathy can occur. A possible disadvantage of a long-term therapy with calcium salts is the development of hypercalcemia which is associated with calcification of blood vessels and soft tissues and gastrointestinal complaints (Dialysis Journal 37 (1991), 1–40).

In addition Burt, H. M. et al. (J. Pharm. Sci. 75 (1987), 379–383) describe anion exchangers which carry tertiary or quatemary amines as the functional group and adsorb inorganic phosphate in the intestinal tract. However, it is known that strongly basic anion exchangers such as for example cholestyraniine (Johns, W. H., Bates, T. R., J. Pharm. Sci 59 (1970), 788 ff.) may also undesirably bind bile acids and hence their long-term use leads to hypovitaminosis.

A common treatment for phosphorus retention is disclosed in U.S. Pat. No. 4,870,105, entitled Phosphorus binder, which discloses a calcium acetate phosphorus binder for oral administration to an individual for the purpose of inhibiting gastrointestinal absorption of phosphorous. It further discloses a method of inhibiting gastrointestinal absorption of phosphorous, comprising administering orally the calcium acetate phosphorus binder, preferably close in time to food and beverage consumption. However, side effects of calcium acetate may include acetic acid breath, stomach upset and gastrointestinal discomfort. Other alternatives for treating phosphorus retention are shown in the following United States patents. U.S. Pat. No. 6,160,016 entitled Phosphorus binder, discloses a calcium formate composition for oral administration to an individual for the purpose of inhibiting gastrointestinal absorption of phosphorous. It further discloses a method of inhibiting gastrointestinal absorption of phosphorous, comprising administering orally the composition, preferably close in time to food and beverage consumption. U.S. Pat. No. 6,103,709 entitled. Therapeutically effective $1\alpha,25$-dihydroxyvitamin D3 analog, discloses a method for treatment of diseases caused by deficiency or overproduction of the vitamin $D_3$ metabolites by administering analogues of $1\alpha,25$-dihydroxyvitamin $D_3$. These are disclosed to be analogues that are selective agonists or antagonists for the genomic and rapid nongenomic cellular responses. It further discloses a pharmaceutical composition comprising $1\alpha,25$-dihydroxyvitamin $D_3$ analog. U.S. Pat. No. 5,939,406 entitled 18-substituted-19-nor-vitamin D compounds, discloses a class of vitamin D compounds, namely, 13-ethyl and 13-vinyl-18,19-dinor-vitamin D derivatives, as well as a general method for their chemical synthesis. The compounds have the formula: $C_{17}H_{22}RR_6Y_1Y_2$, where $Y_1$ and $Y_2$, which may be the same or different, are each selected from the group consisting of hydrogen and a hydroxy-protecting group, $R_6$ is selected from the group consisting of an ethyl or vinyl radical, and where the group R represents any of the typical side chains known for vitamin D type compounds. These 18-substituted compounds are characterized by minimal intestinal calcium transport activity and minimal bone calcium mobilization activity resulting in novel therapeutic agents for the treatment of second hyperparathyrodism. These compounds also are disclosed as exhibiting pronounced activity in arresting the proliferation of undifferentiated cells and inducing their differentiation to the monocyte thus evidencing use as anti-cancer agents and for the treatment of diseases such as psoriasis. U.S. Pat. No. 5,753,706 entitled Methods for treating renal failure, discloses a method of controlling phosphate metabolism and metabolic acidosis in patients suffering from renal failure and associated hyperphosphatemia or patients predisposed to development of a hyperphosphatemic condition. The method comprises administering to a patient a ferric-containing compound selected from the group consisting of ferric citrate, ferric acetate, and combinations thereof. It discloses that a therapeutic benefit can be realized in accordance with such method by administering the compound orally to a patient to contact and bind with ingested phosphate in the patient's digestive tract, and thereby prevent its intestinal absorption. U.S. Pat. No. 5,597,815 entitled Prevention of hyperphosphatemia in kidney disorder patients, discloses that 19-nor-vitamin D analogs, and particularly 19-nor-$1\alpha,25$-dihydroxyvitamin $D_2$, possess low calcemic and phosphatemic activity while also having the ability to suppress parathyroid hormone (PTH) production. It further discloses that the suppressive effect on PTH secretion of these 19-nor analogs without significant changes in serum calcium or serum phosphorus make them ideal tools for the treatment of secondary hyperparathyroidism in patients having kidney disorders. U.S. Pat. No. 4,308,264, entitled Stabilized, dilute aqueous preparation of $1\alpha,25$-dihydroxycholecalciferol for neonatal administration, discloses $1\alpha,25$-Dihydroxycholecalciferol, also known as $1\alpha,25$-dihydroxyvitamin $D_3$, calcitriol or $1\alpha,25(OH)_2D_3$, that occurs naturally in man as the active form of cholecalciferol or vitamin $D_3$. It further discloses that the natural supply of vitamin $D_3$ depends on the conversion of 7-dehydrocholesterol to vitamin $D_3$ in the skin by ultraviolet light. Vitamin $D_3$ is then converted to calcitriol in a two-step process in the liver and kidney before its acts on its target issue. U.S. Pat. No. 6,103,126, entitled Process for the selective elimination of inorganic phosphate from liquids by means of absorbent materials modified with polynuclear metal oxhydroxides, discloses the use of an adsorbent material modified with polynuclear metal oxhydroxides for the selective elimination of inorganic phosphate from liquids, in particular from body fluids containing protein such as whole blood, plasma, liquid contents of the intestine as well as from dialysis fluid, as well as a process for the production of a pharmaceutical agent for oral application for the selective removal of inorganic phosphate in which an adsorbent material used is coated with a layer resistant to gastric acid or dispensed into an acid-resistant capsule. It further discloses that in order to selectively eliminate inorganic phosphate in an extracorporeal perfusion system, a body fluid such as whole blood or plasma is passed over one of the adsorbent materials. U.S. Pat. No. 4,689,322, entitled Phannaceutical products, calcium mixed salts of polymeric, anionic carboxylic acids and/or their esters of sulfuric acid, and methods for their preparation and use, discloses a pharmaceutical product which contains at least a calcium salt or a calcium mixed salt of a natural or chemically modified polymeric, anionic carboxylic acid and/or an ester of sulfuric acid, and additive materials and/or an ester of sulfuric acid, and additive materials and/or carrier materials. There are further disclosed calcium salts, and methods of preparation thereof, comprised of polymannuronic acid, polygalacturonic acid, polyglucuronic acid, polyguluronic acid, the oxidation products of homoglycans, the oxidation products of heteroglycans, or their mixtures, for controlling the levels of phosphate, calcium and iron in patients with chronic uremia and/or the control of the oxalate and/or phosphate of the blood in kidney stone prophylaxis.

It would be very useful to have a phosphorus binder available which does not have the risks associated with ingestion, acetic acid breath and other short comings of some presently available binders. The binder should be more efficient in binding phosphorus and, thus, would not have to be consumed in the large quantities necessary, for example, when calcium carbonate-containing compositions are used. Such a phosphorus binder would be particularly valuable for administration to individuals with chronic renal failure, in whom phosphorus retention is a serious concern and the risk of toxicity from consumption of presently-available binders may be greater than in individuals in whom kidney function is normal.

There is thus recognized in the medical community an urgent need for the development of a phosphate binder efficient and safe in binding phosphate in renal failure. Accordingly, it is one object of this invention to provide a composition and method for controlling hyperphosphatemia and phosphate retention utilizing a phosphate binding compound. It is another object of this invention to provide a composition and method for correcting metabolic acidosis in renal failure. It is yet another object of this invention to provide a composition and method in an oral dosage form for inhibiting the absorption of dietary phosphate and/or correcting metabolic acidosis. It is yet another object of the invention to provide a calcium supplement that is highly soluble to increase its bioavailability to help prevent osteoporosis.

Other features and advantages of the present invention will become apparent from the following description and appended claims.

SUMMARY OF THE INVENTION

A method for inhibiting gastrointestinal absorption of phosphorous in an individual, comprising orally ingesting a quantity of calcium glutarate sufficient to bind with phosphorous in the gastrointestinal tract. The calcium glutarate is present in an amount sufficient to provide between about 400 mg to about 1500 mg of calcium as calcium glutarate. The calcium glutarate may be in tablet form, gelatin capsule form, effervescent form or in liquid form. The calcium glutarate may be administered at mealtime. An orally administerable pharmaceutical composition is used in the treatment of hyperphosphatemia and for preventing the formation of phosphate- and oxalate-containing kidney stones which comprises as the principal active ingredient a therapeutically effective amount of calcium glutarate combined with a pharmaceutically acceptable carrier in the form of beads, tables, liquid, capsules, powders, dragees or pills.

DETAILED DESCRIPTION OF THE PREFERRED EMBODIMENTS

The invention relates to a compound and a method of controlling serum phosphate levels and metabolic acidosis in patients suffering from renal failure and associated hyperphosphatemia or patients predisposed to development of a hyperphosphatemic condition. The method in accordance with this invention comprises administering to a patient a calcium glutarate compound. Therapeutic benefit can be realized in accordance with such method by administering the compound orally to a patient to bind ingested phosphate in the patient's digestive tract, and thereby prevent intestinal absorption.

In a preferred embodiment of this invention, the calcium glutarate compounds are formulated as a therapeutic dosage form for oral administration to a patient afflicted with hyperphosphatemia or predisposed to develop that condition. Thus, the calcium glutarate compounds can be formulated as an effervescent, liquid or gel suspension, or in a unitary solid dosage form such as a compressed tablet or capsule. Methods and excipients for preparation of both gel and solid dosage forms are well known in the art. It will be appreciated that the composition of the present invention may also be employed in any other pharmaceutically acceptable form. While calcium glutarate is relatively expensive to manufacture because of the high cost of materials, this disadvantage is out weighed by its many advantages.

The oral dosage form should be formulated to contain sufficient calcium glutarate compound to bind, upon ingestion by the patient, sufficient ingested phosphate in the patient's intestinal tract to inhibit the absorption of ingested phosphate and thereby reduce the probability of either the development of a hyperphosphatemic condition or the complication of an already existing hyperphosphatemic condition. Thus, each oral dose of the therapeutic calcium glutarate composition in accordance with this invention can contain from about 400 mg to about 1500 mg of calcium as calcium glutarate. A therapeutically-effective amount of the calcium glutarate compounds to be administered will depend on the severity of the patient's condition, the nature of the patient's diet and the binding capacity of the calcium glutarate compound used in the formulation. By "therapeutically-effective amount" is meant an amount effective to achieve a selected desired result in accordance with the present invention, without undue adverse physiological effects or side effects; the desired result generally being a clinically observable reduction in absorption of ingested phosphate and/or a correction in metabolic acidosis. The dosages of the compounds to be administered in accordance with this invention can thus be altered, if necessary, to correspond to the level of phosphate binding required in the patient's digestive tract. A daily dosage of about 400 mg to about 1500 mg of calcium as calcium glutarate is expected to be effective. However the dosage depends on the patient and accordingly may be less or more than the above stated dosage. The solubility is about 5.2 gm per 100 cc. Calcium gluconate and calcium lactate also have high solubilities but only have about 9 per cent and 13 per cent elemental calcium, respectively.

Calcium glutarate has numerous advantages. It is highly soluble which makes is readily bioavailable. This is more significant in patients that do not secrete much stomach acid to convent insoluble forms. The high solubility makes calcium glutarate readily bioavailable to the patient so that it makes the calcium available and can bind phosphates. Calcium glutarate also does not form harmful complexes.

The calcium glutarate has a density of about 0.65 gm/cc. It has about 21.6 per cent elemental calcium. Its formula is [OOC—$CH_2$—$CH_2$—$CH_2$—COO]Ca. The reaction for the formation of calcium glutarate is:

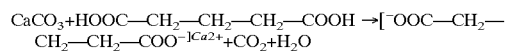

The calcium glutarate can be made using FDA good manufacturing practices by taking a quantity of USP/FCC grade calcium containing compound such as calcium carbonate, calcium hydroxide or calcium oxide and mixing it with a quantity of high purity glutaric acid in a ribbon mixer. A batch example might include 14 Kg of calcium and 19 Kg of glutaric acid. Mixing for about 2–3 minutes then follows. Purified water, USP, in the amount of about 15 Kg is added to the mixer and mixed for about 20–30 minutes. The mixture is then transferred to trays and dried overnight for about 12–18 hours at 65–85 degrees Centigrade. The dried compound is then milled and passed through a 0.079 inch screen, to yield a granular material acceptable for pharmaceutical processing in the manufacture of tablets or capsules. It is then processed to form the final product.

Calcium bioavailability, or the amount of calcium available for intestinal absorption, may vary among different calcium salts. Variations result from differing properties such as the low aqueous solubility of some salts (calcium carbonate and calcium phosphate) and the ability of some anionic components (such as citrate) to form soluble complexes with calcium. The aqueous solubility of many calcium salts decreases as pH increases. In the normally acid environment of gastric juice, most calcium salts, even if relatively insoluble, dissolve and become bioavailable except at very high dosages. However, when gastric acidity is abnormally low resulting in a high pH (as in achlorhydria or in some elderly persons who have defective acid production), calcium bioavailability from calcium carbonate and calcium phosphate may be low because of their incomplete gastric dissolution. When calcium salts of lactate, citrate and carbonate are given, the anions released may tend to neutralize the gastric juice and impair further solubility of calcium salts. Calcium solubility may also depend on the type and extent of soluble complexation of calcium. The calcium complex (such as calcium glutarate) itself is believed to be highly soluble and readily absorbable. Thus, in patients with impaired efficiency of intestinal calcium absorption, the provision of calcium supplementation with a high bioavailability and solubility due to particular chemical form should facilitate correction of physiologically abnormal calcium absorption, thus be available for phosphate binding.

However, calcium supplementation may cause the undesirable side effect of calciumcontaining kidney stones, especially in persons with relatively normal intestinal calcium absorption. An optimum calcium supplement should exhibit superior calcium bioavailability in order to best avert negative calcium balance, and should also reduce the risk for kidney stone formation. Thus, a it is desirable to provide efficiently absorbed calcium while precluding calcium nephrolithiasis.

The following in-vitro tests were conducted to test the solubility and ability of calcium glutarate to bind with phosphates. The tests included analysis for monobasic, $Ca(Na_2PO_4)_2$, dibasic, $CaNaPO_4$, and tribasic, $Ca(PO_4)_2$ binding. The three examples are as follows.

EXAMPLE 1

An aqueous solution of calcium glutarate was mixed with a twice over molar solution of sodium phosphate. A suspension formed which was filtered by a vacuum through a 0.45-$\mu$m nylon filter. The resulting filtrate was assayed for free calcium by atomic absorption spectrometry. The percent of calcium recovered in solution was 0.1%. The test showed that almost all of the calcium was in the practically insoluble form of calcium phosphate.

EXAMPLE 2

An aqueous solution of calcium glutarate was mixed with an equi-molar solution of sodium phosphate. A suspension formed which was filtered by vacuum through a 0.45-$\mu$m nylon filter. The resulting filtrate was assayed for free calcium by atomic absorption spectrometry. The percent of calcium recovered in solution was 0.1%. The test indicated that almost all of the calcium was in the practically insoluble form of calcium phosphate.

EXAMPLE 3

An aqueous solution of calcium glutarate was mixed with a two-thirds molar solution of sodium phosphate. A suspension formed which was filtered by vacuum through a 0.45-$\mu$m nylon filter. The resulting filtrate was assayed for free calcium by atomic absorption spectrometry. The percent of calcium, recovered in solution was 4.5%. The test indicated that almost all of the calcium was in the practically insoluble form of calcium phosphate.

Calcium glutarate does not appear to form undesirable complexes. It has a pleasant taste so it can be taken in the form of a tablet, or it may be taken as a liquid. Because of the ability of the calcium glutarate to easily and rapidly bind with the phosphates a relative small dosage is possible under usual circumstances. Calcium glutarate has the qualities that are desirable in binding phosphates. It is highly soluble so it should be effective even when there is little stomach acid. Virtually all of the calcium glutarate would appear to readily bind with available phosphates to form insoluble salts that can be passed through a patient's digestive system. A reasonable excess of calcium glutarate beyond that needed to bind with free phosphates would appear to pose no problem and would be available to provide calcium to treat or prevent osteoporosis or other diseases that are treated with calcium supplements. It would also appear to not be a risk for the formation of kidney stones.

We claim:

1. A method of inhibiting gastrointestinal absorption of phosphorous in a person, comprising: orally administering to a person in need thereof a quantity of a pharmaceutical composition of calcium glutarate sufficient to bind with phosphorous in the gastrointestinal tract, wherein said pharmaceutical composition inhibits gastrointestinal absorption of phosphorous in the person, and wherein said composition does not contain non-glutarate calcium salts in amounts sufficient to neutralize gastric acidity.

2. The method according to claim 1 wherein the calcium glutarate is present in an amount sufficient to provide between about 400 mg to about 1500 mg of calcium as calcium glutarate.

3. The method according to claim 1 wherein the calcium glutarate is in tablet form.

4. The method according to claim 1 wherein the calcium glutarate is in gelatin capsule form.

5. The method according to claim 1 wherein the calcium glutarate is in liquid form.

6. A method of inhibiting gastrointestinal absorption of phosphorous in an individual, comprising: orally administering to a person in need thereof a quantity of a pharmaceutical composition of calcium glutarate sufficient to bind with phosphorous in the gastrointestinal tract at a mealtime, wherein said pharmaceutical composition inhibits gastrointestinal absorption of phosphorous in the person, and wherein said composition does not contain non-glutarate calcium salts in amounts sufficient to neutralize gastric acidity.

7. The method according to claim 6 wherein the quantity of calcium glutarate is present in an amount sufficient to provide between about 400 mg to about 1500 mg of calcium as calcium glutarate.

8. The method according to claim 6 wherein the quantity of calcium glutarate is in tablet form.

9. The method according to claim 6 wherein the quantity of calcium glutarate is in gelatin form.

10. The method according to claim 6 wherein the calcium glutarate is in liquid form.

11. A pharmaceutical therapeutic composition in solid or gel oral dosage form for controlling phosphate retention in patients having need for reduced absorption of dietary phosphate, said oral dosage form composition comprising sufficient calcium glutarate to bind with phosphorous in the gastrointestinal tract, and a pharmaceutically acceptable excipient for said oral dosage form, wherein said solid or gel oral dosage form comprises a single dose, and wherein said composition does not contain non-glutarate calcium salts in amounts sufficient to neutralize gastric acidity.

12. The therapeutic composition according to claim 11 wherein the quantity of calcium glutarate is present in an amount sufficient to provide between about 400 mg to about 1500 mg of calcium as calcium glutarate.

13. The therapeutic composition according to claim 11 wherein the quantity of calcium glutarate is in tablet form.

14. The therapeutic composition according to claim 11 wherein the quantity of calcium glutarate is in gelatin form.

15. An orally administerable pharmaceutical composition for use in the treatment of hyperphosphatemia and for reducinig the risk of the formation of phosphate- and oxalate-containing kidney stones in humans which comprises as the principal active ingredient a therapeutically effective amount of calcium glutarate sufficient to bind with phosphorous in the gastrointestinal tract combined with a pharmaceutically acceptable carrier, wherein said pharmaceutical composition comprises, solid or gel oral dosage of a single dose, and wherein said composition does not contain non-ghitarate calcium salts in amounts sufficient to neutralize gastric acidity.

16. A pharmaceutical composition according to claim 15 particularly adapted for treating hyperphosphatemia and for reducing the risk of the formation of phosphate- and oxalate-containing kidney stones in which the calcium glutarate is present in the amount of about 400 mg to about 1500 mg of calcium as calcium glutarate.

17. A method for treating hyperphosphatemia and for reducing the risk of the formation of phosphate- and oxalate-containing kidney stones in humans which comprises orally administering to a person in need thereof a pharmaceutical composition according to claim 16.

18. A method of treating hyperphosphatemia and for reducing the risk of the formation of phosphate-containing kidney stones in humans which comprises orally administering to a person in need thereof a pharmaceutical composition according to claim 16.

19. A method of treating hyperphosphatemia and for reducing the risk of the formation of phosphate- and oxalate-containing kidney stones in humans which comprises orally administering to a person in need thereof a pharmaceutical composition according to claim 15.

20. A method of treating hyperphosphatemia and for reducing the risk of the formation of phosphate-containing kidney stones in humans which comprises orally administering to a person in need thereof a pharmaceutical composition according to claim 15.

21. A pharmaceutical compound for treating hyperphosphatemia and for reducing the risk of the formation of phosphate-containing kidney stones in humans of the formula: pharmaceutical grade [OOC—$CH_2$—$CH_2$—$CH_2$—COO]Ca in an amount sufficient to inhibit gastrointestinal absorption of phosphorous in a person, and a pharmaceutically acceptable carrier, wherein said pharmaceutical composition comprises a solid or gel oral dosage of a single dose, and wherein said composition does not contain non-glutarate calcium salts in amounts sufficient to neutralize gastric acidity.

22. A method of treating hyperphosphatemia and for reducing the risk of the formation of phosphate-containing kidney stones in mammals, which comprises administering to a mammal a phosphorous binding amount of the compound of claim 21.

23. A method of treating hyperphosphatemia, which comprises administering to a mammal a hyperphosphatemia treating amount of the compound of claim 21.

24. A therapeutic composition according to claim 21 wherein the quantity of calcium glutarate is present in an amount sufficient to provide between about 400 mg to about 1500 mg of calcium as calcium glutarate.

25. The therapeutic composition according to claim 21 wherein the quantity of calcium glutarate is in tablet form.

26. The therapeutic composition according to claim 21 wherein the quantity of calcium glutarate is in gelatin form.

* * * * *